United States Patent [19]
Hooke et al.

[11] Patent Number: 5,661,247
[45] Date of Patent: Aug. 26, 1997

[54] ROTATIONAL DISPLACEMENT APPARATUS WITH ULTRA-LOW TORQUE AND HIGH THRUST LOAD CAPABILITY

[75] Inventors: David Andrew Hooke, Smyrna; Erian A. Armanios, Marietta, both of Ga.

[73] Assignee: Georgia Tech Research Corporation, Atlanta, Ga.

[21] Appl. No.: 562,586

[22] Filed: Nov. 24, 1995

[51] Int. Cl.$^6$ ...................................................... G01N 3/22
[52] U.S. Cl. ........................... 73/847; 73/800; 73/862.191
[58] Field of Search ............................... 73/800, 826, 837, 73/847, 862.191, 862.324, 862.328

[56] References Cited

U.S. PATENT DOCUMENTS

| | | | |
|---|---|---|---|
| 3,796,519 | 3/1974 | Marceau | 417/294 |
| 4,055,080 | 10/1977 | Farr et al. | 73/862.31 |
| 4,446,746 | 5/1984 | Aoshima et al. | 73/862.324 |
| 5,005,424 | 4/1991 | Markowski | 73/837 |

FOREIGN PATENT DOCUMENTS

| | | | |
|---|---|---|---|
| 158710 | 8/1990 | U.S.S.R. | 73/847 |

OTHER PUBLICATIONS

Examination of Three Methods for Testing Extension–Twist Coupled Laminates, Hooke, et al. with the School of Aerospace Engineering, Georgia Institute of Technology, (Sep. 1996).

*Primary Examiner*—George M. Dombroske
*Assistant Examiner*—Max H. Noori
*Attorney, Agent, or Firm*—Isaf, Vaughan & Kerr

[57] ABSTRACT

This invention comprises an improved rotational displacement apparatus for measuring accurately the twist induced in an extension-twist coupled specimen in response to application of an axial load. The apparatus has an internal cylinder within which a piston rides. A piston rod extends from the piston through a pair of radial ball bearings in the base of the cylinder block to a free end outside the cylinder block. The piston is sized to be slightly smaller in diameter than the cylinder to provide a small space between the piston and the cylinder walls. Means for supplying compressed air to the region of the cylinder below the piston and means for venting air from the region of the cylinder above the piston are provided. An optical encoder is coupled to measure rotational motion of the piston within the cylinder. In use, the apparatus is mounted in a testing machine and a specimen to be tested is secured at one end to the free end of the piston rod and at its other end to the mounting block of the testing machine. Compressed air is then supplied to the cylinder causing the piston to ride up in the cylinder to apply an axial load to the test specimen. The piston rides on a cushion of compressed air and is free to rotate virtually friction free. Thus, any twist induced in the specimen as a result of the axial load causes the piston to rotate and this rotation is measured by the optical encoder.

12 Claims, 1 Drawing Sheet

ROTATIONAL DISPLACEMENT APPARATUS WITH ULTRA-LOW TORQUE AND HIGH THRUST LOAD CAPABILITY

STATEMENT OF GOVERNMENT LICENSE RIGHTS

The U.S. Government has a paid-up license in this invention and the right in limited circumstances to require the patent owner to license others on reasonable terms as provided for by the terms of contract number DAAL03-92-G03A0 awarded by the U.S. Army.

TECHNICAL FIELD

The present invention relates generally to measuring devices and more specifically to an improved apparatus for measuring extension-twist coupling in any specimen exhibiting extension-twist coupling such as, but not limited to, flat or twisted isotropic or anisotropic specimens. The apparatus of this invention is designed to apply an axial load to such a specimen and to measure the twisting response accurately.

BACKGROUND OF THE INVENTION

Elastically tailored composite laminates are laminates that have been designed with specifically tailored stiffness parameters. These parameters can be sized to give an out-of-plane response to an in-plane loading, resulting in deformation modes not found in conventional isotropic materials. Two examples of elastically tailored composite laminates are those that exhibit bend-twist coupling and those that exhibit extension-twist coupling. A bend-twist coupled laminate will twist about its longitudinal axis when a lateral bending moment is applied thereto. Such laminates have application in fixed wing structures of aircraft where an increase in wing loading may produce a wing-tip wash-in to help prevent tip stall.

An extension-twist coupled laminate will twist about its longitudinal axis when an axial force is applied thereto. Extension-twist coupled laminates have application in rotary wings such as the rotors of helicopters where an increase in centrifugal load can result in an increase or decrease in the pitch angle of the rotor blade. Pretwisted strips made of isotropic materials such as metals exhibit extension-twist coupling as they tend to untwist when subjected to axial force. The present invention is concerned with these extension-twist coupled strips and laminates.

When designing extension-twist coupled specimens, it is imperative that the stiffness characteristics of the specimens be determined accurately. That is, it must be known accurately how much twist is induced in the specimen when a known axial load is applied. In the past, experimental methods to determine the extension-twist characteristics of a specimen have relied on specialized test apparatuses built for a narrow field of use. One such apparatus used a suspended weight applied through a thrust bearing and reflected laser light beams to determine the twist distribution of the test specimen. While the measurements were accurate, higher loads were not attempted and the apparatus required a good amount of support equipment.

In instances where a higher axial load has been required to induce the twist to be measured, suspended weight measuring machines are not feasible. In these instances, conventional servohydraulic bi-axial testing machines may be used. Such machines function through the use of hydraulic actuators and load cells. For a tension-torsion servohydraulic testing machine, there are two hydraulic actuators, one for axial load application and one for torque application. Similarly, there are two load cells; one to measure the axial load and one to measure the torque. Closed loop control is made by comparing the load cell feedback to the commanded control signal. With a tuned system, axial load and torque can be applied and controlled. In the case of the extension-twist coupled specimens, it is desirable to know what the twist response is due to an applied axial load. Implicit in that statement is that at least one end of the test specimen is free to twist. A hi-axial test machine would be programmed to load axially while maintaining the zero torque condition required by free twist. However, in the case of specimens with low torsional rigidity, such as extension-twist coupled laminates, the torsional rigidity is lower than the noise threshold for torsion load cells and the torque actuator does not receive the correct feedback signal, resulting in a perceived stiffening of the specimen. An accurate survey of the stiffness properties is therefore not possible.

Thus, there exists a need for an improved method and apparatus for measuring the twist versus axial load characteristics of an extension-twist coupled specimen. Such a method and apparatus should allow free twisting as an axial load is applied with zero or negligible torsional resistance to the twisting motion because of friction. Further, the resistance should remain zero or negligible as ever increasing axial force is applied, even to the point where the specimen experiences actual structural failure. Preferably, the apparatus should incorporate reliable, accurate, and repeatable means for measuring the amount of twist induced in the specimen as a function of the applied axial force. The device should be simple in construction and operation, should be able to be produced and marketed for an affordable cost, and should be directly usable in its own load frame or incorporated with an existing load frame. It is to the provision of such a method and apparatus that the present invention is primarily directed.

SUMMARY OF THE INVENTION

The present invention, in one preferred embodiment thereof, comprises an ultra-low torque, ultra-low friction rotational displacement apparatus and axial thrust load applicator for measuring the twist versus axial force characteristics of an extension-twist coupled specimen. The invention comprises a main cylinder block defining an internal cylinder, a top plate covering the cylinder and having a projecting threaded boss for connecting the apparatus to testing equipment, and a bottom plate mounted to the bottom of the cylinder block. A piston is movably mounted in the cylinder and an associated piston rod extends from the piston through the bottom of the cylinder block and bottom plate to a free end. The piston rod is rotatably journaled in a pair of radial ball bearings, which prevent lateral movement of the piston rod while permitting the piston rod and piston to rotate freely within the cylinder.

A pressurized air inlet is provided through the bottom plate and communicates with a thin plenum formed between the bottom plate and the bottom of the cylinder block. An array of ports is formed in the bottom of the cylinder block to deliver pressurized air from the plenum into the cylinder in the region below the piston. A vent duct is provided through the top plate covering the cylinder block and communicates between the interior of the cylinder and the atmosphere.

The diameter of the piston is slightly less than the diameter of the cylinder in which it rides so that there is no physical contact between the piston and the cylinder walls.

Thus, the piston is free to rotate within the cylinder with only the negligible friction of the radial ball bearings to resist such rotation.

A gear shaft is rotatably journaled within a pair of radial ball bearings in the center of the top plate and extends downwardly therefrom along the axis of the cylinder to a free end. The lower portion of the gear shaft is machined to form a hexagonal rod that is slidably journaled within a corresponding hexagonal sleeve extending through the top of the piston along its central axis. With this configuration, when the piston rides up and down within the cylinder, the rod slides up and down on the sleeve. However, any rotational movement of the piston within the cylinder is transferred to the gear shaft through the mated rod and sleeve.

A first gear is mounted on the gear shaft adjacent to the top of the cylinder and rotates therewith. The first gear is operatively mated to a second gear that is mounted on an encoder shaft that, like the gear shaft, is rotatably journaled within a pair of radial ball bearings fixed in the top cover of the cylinder. The free end of the encoder shaft is rotatably coupled to an optical encoder adapted to detect rotational movement of the encoder shaft to a predetermined accuracy and produce an electrical signal indicative of the detected movement. The electrical signal is transmitted out of the cylinder block by appropriate conductors that are in turn coupled to an electronic device for interpreting the electrical signals and displaying the degree of piston rotation corresponding thereto.

In use, the apparatus and axial load applicator of this invention is mounted by its threaded boss to the top mounting block of a standard uni-axial or other type testing machine with the piston rod of the apparatus extending downwardly. An appropriate specimen grip is secured to the free end of the piston rod and a similar grip is secured to the lower mounting block of the testing machine. A test specimen in the form of an elongated strip is secured at its ends to the specimen grips.

With the specimen and apparatus thus mounted, compressed air is supplied through the inlet of the apparatus. The air enters the thin plenum between the bottom cover of the apparatus and the bottom of the cylinder block and, in turn, is delivered through the array of ports to the interior of the cylinder below the piston. The resulting pressure differential between the bottom of the piston and its top causes the piston to move within the cylinder on a cushion of compressed air until the specimen is pulled taught. Since there is a small space between the piston and the cylinder wall, the compressed air slowly escapes around the piston to the top portion of the cylinder where it is vented to the atmosphere through the vent duct.

As the pressure of the supplied air increases, the piston and piston rod exert a correspondingly increasing axial force on the test specimen. Consequently, the specimen, because of its extension-twist coupled nature, twists in response to the axial force. Since the piston rides on a cushion of air, it is free to rotate with the twisting specimen, resisted only by the negligible friction of the radial ball bearings in which the various shafts are journaled. This friction does not change with increased air pressure and corresponding increased axial force. Thus, very large axial forces can be applied to the specimen and the specimen remains free to twist in response.

As the specimen twists causing the piston rod and piston to rotate within the cylinder, this rotational motion is transferred through the gear shaft, the first and second gears, and the encoder shaft to the optical encoder. The encoder, in turn, detects the rotation of the encoder shaft and transmits a corresponding signal to the electrical interpreting device, which can be calibrated to read out directly the angle through which the piston rod and piston have rotated and thus the magnitude of twist induced in the test specimen in response to the applied axial force.

Thus, it is seen that an improved rotational displacement apparatus is now provided that addresses the problems and shortcomings of prior art. The apparatus of this invention allows for accurate repeatable measurement of the twist versus axial load characteristics of extension-twist coupled specimens. The apparatus itself supplies the axial load as the piston is forced upward in its cylinder through the application of compressed air. As increased axial load is applied, the specimen is free to rotate in response because the apparatus of this invention offers virtually no torsional resistance to such rotation and is therefore superior to prior art devices. Finally, the apparatus of this invention can be produced and used economically in conjunction with existing uni-axial load machines or incorporated as a part of a stand alone load frame. These and other objects, features, and advantages will become more apparent upon review of the detailed description set forth below taken in conjunction with the accompanying drawing figure, which is briefly described as follows.

DETAILED DESCRIPTION OF THE PREFERRED EMBODIMENT

Figure 1:
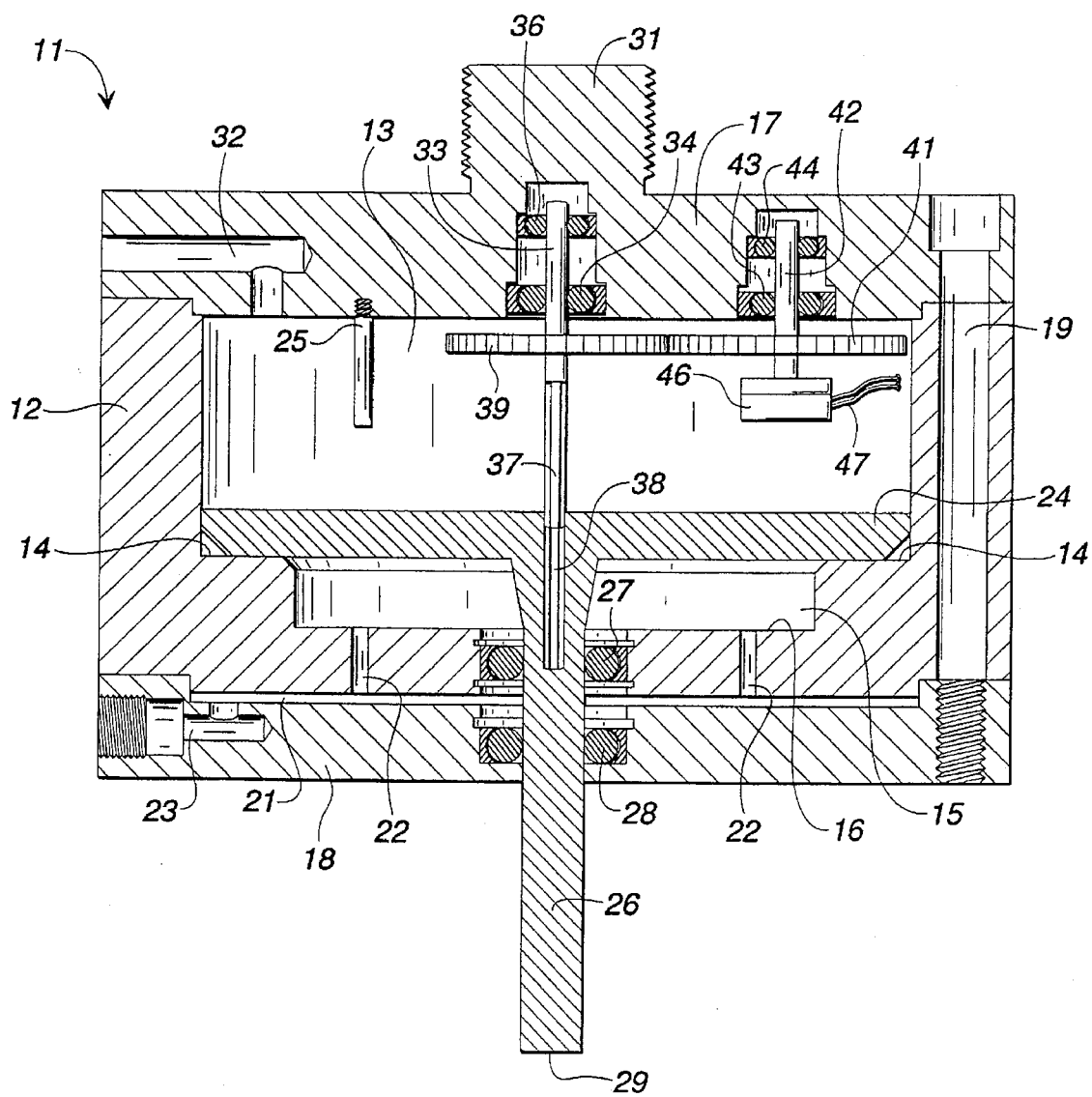
FIG. 1 is a partially sectioned side elevation view of a rotational displacement apparatus that embodies principles of the present invention in a preferred form.

Referring now in more detail to the drawing, in which the various component parts are identified by reference numbers, FIG. 1 illustrates in a partially sectioned view a rotational displacement apparatus that embodies principles of this invention in a preferred form. The apparatus 11 comprises a main cylinder block 12, preferably formed of machined steel. The cylinder block 12 defines an internal cylinder having a cylinder wall 13, an annular lip 14, a lower well portion 16, and a floor 15. A generally disk-shaped top plate 17 covers the main cylinder block 12 and closes off the top of the cylinder. Similarly, a generally disk-shaped bottom plate 18 covers the bottom of the main cylinder block 12. The main cylinder block 12, top plate 17, and bottom plate 18 are securely held together by a plurality of appropriate bolts 19, which preferably are arrayed around the periphery of the apparatus 11.

The bottom plate 18 is machined so that when it is mounted on the bottom of the main cylinder block 12, a thin plenum 21 is defined between the bottom of the cylinder block and the bottom plate 18. A plurality of inlet ports 22 are formed through the bottom of the main cylinder block and preferably are configured in a circular array about the central axis of the cylinder block. The inlet ports communicate between the thin plenum 21 and the lower well portion 16 of the cylinder. A compressed air supply coupling 23 communicates with the thin plenum 21 and provides for the delivery of compressed air from an external source to the plenum 21 for purposes described in more detail hereinbelow.

A piston 24 is disposed within the internal cylinder of the main cylinder block 12. The piston 24 includes a piston rod 26 that projects downwardly from the center of the piston through the bottom of the main cylinder block and the bottom plate. The piston rod is rotatably and slidably journaled within a first radial ball bearing 27 disposed in the bottom of the cylinder block 12 and a second radial ball bearing 28 disposed within the bottom plate 18. The piston rod 26 extends downwardly from the main body portion of the apparatus 11 to a free end 29. With the just described arrangement, it will be seen that the piston 24 and piston rod 26 are free to slide up and down within the cylinder defined by the main cylinder block 12 with the piston rod 26 sliding within the radial ball bearings 27 and 28. At the same time, the piston 24 and piston rod 26 are free to rotate about their central axis with negligible torsional friction because of the radial ball bearings 27 and 28.

The piston 24 has a diameter that is slightly less than the diameter of the cylinder in which it rides so that a small space is defined between the piston 24 and the cylinder wall 13. In this way, the piston 24 does not engage or contact the cylinder wall as it rides up and down or rotates within the cylinder. Radial ball bearings 27 and 28 secure the piston rod against lateral movement while at the same time allowing it to slide and rotate freely.

The top plate 17, which covers and closes off the cylinder, is provided with an upwardly projecting threaded boss 31 for mounting the apparatus 11 securely within a testing machine. A vent duct 32 is machined in the top plate 17 and communicates between the upper region of the cylinder and the atmosphere. A downwardly extending column 25 projects from the top plate and prevents the piston 24 from rising too far within the cylinder.

A gear shaft 33 is rotatably journaled within a pair of radial ball bearings 34 and 36, which, in turn, are mounted within the top plate 17 of the apparatus 11. The gear shaft 33 extends downwardly from the top plate 17 along the axis of the cylinder, piston, and piston rod. The lower portion 37 of the gear shaft 33 is machined with a generally hexagonal crossesection that defines a hex rod extending downwardly along the axis of the apparatus. A corresponding hexagonal sleeve 38 is machined in the piston and piston rod extending along the central axis thereof. The sleeve 38 is sized, configured, and positioned to receive the hexagonal rod formed on the bottom portion 37 of the gear shaft 33. With this configuration, it will be seen that as the piston 24 rides up and down within the cylinder, the rod 37 moves correspondingly in and out of the sleeve 38. Further, when the piston 24 rotates within the cylinder, this rotational motion is transferred to the gear shaft 33, causing it to rotate within its radial ball bearings 34 and 36. Thus, free axial movement of the piston is allowed while rotational movement of the piston is transferred to the gear shaft 33.

A first gear 39 is securely mounted on the gear shaft 33 near the top of the cylinder defined in the cylinder block 12. The first gear 39 is fixed to the shaft 33 so that the gear 39 and the shaft 33 rotate together. The first gear 39 is meshed with a second gear 41, which is fixed on an encoder shaft 42 that, in turn, is rotatably journaled within a pair of radial ball bearings 43 and 44. The upper end of the encoder shaft 42 is operatively coupled to a commercial optical encoder 46.

The optical encoder 46 is securely mounted to the top plate 17 and adapted to detect rotation of the encoder shaft 42 and produce an electrical signal corresponding to the degree of rotation detected. This electrical signal is transmitted via appropriate conductors 47 outside of the cylinder block where the conductors are connected to an electronic decoder, which translates the electrical signals into the degree of detected rotation of the encoder shaft and displays the results to a user. Most commercial optical encoders function by counting small closely spaced bands that are provided on the encoder shaft 42. However, other types of encoders might also be used to measure the rotation of the shaft 42. In the present application, it has been found that encoder model MOD5541-25-500-L available from BEI Motion Systems Company is suitable.

In use for measuring the twist versus axial load characteristics of an extension-twist coupled laminate, the apparatus 11 of the present invention is mounted in an appropriate testing machine. For example, when used with a uniaxial testing machine, the threaded boss 31 of the apparatus is threaded within the top mounting block of the machine with the apparatus and piston rod 29 extending downwardly therefrom. An appropriate specimen grip is then secured to the free end 29 of the piston rod and a similar grip is secured to the lower mounting block of the testing machine. A test specimen is then secured at its ends to the specimen grips extending therebetween.

A source of compressed air is coupled to the compressed air supply coupling 23 and the readout of the encoder 46 as well as the readout of the axial load detector, which is a part of the testing machine itself, are appropriately zeroed or otherwise calibrated. Compressed air is then delivered through the coupling 23 to the thin plenum chamber 21. From the plenum chamber 21, the compressed air is evenly distributed through the inlet ports 22 to the lower well portion 16 of the cylinder. This, in turn, causes a pressure differential between the bottom of the piston 24 and the top of the piston 24, thus forcing the piston 24 upwardly within the cylinder.

As the piston 24 begins to rise within the cylinder, the compressed air in the region below the piston escapes slowly through the space between the piston 24 and the piston wall 13. Thus, it can be seen that the piston 24 rides and is supported on a cushion of compressed air so that there is no contact between the piston and the cylinder block. The air that flows between the piston and the piston wall is vented to the atmosphere through the vent duct 32, thus maintaining the pressure differential between the bottom of the piston and the top of the piston.

Increasing air pressure in the region of the cylinder below the piston begins to exert an axial force on the specimen mounted in the testing machine. As the axial force increases, the specimen twists in response to the applied force. Since the piston 24 rides on a cushion air within the cylinder and does not touch the cylinder walls, the piston rod and piston are free to rotate with the twisting specimen. The only frictional resistance to this rotational motion is the inherent resistance of the various radial ball bearings, which is negligible for these purposes. As the piston and piston rod rotate with the twisting specimen, the rotation is transferred through the gear shaft 33 and gears 39 and 41 to the optical encoder shaft 42. Thus, rotation of the piston 24 results in a corresponding rotation of the optical encoder shaft 42. This rotation, in turn, is measured by the optical encoder 46 and a signal corresponding to the measured rotation is produced and transmitted via the conductors This signal is then decoded by an appropriate decoder (not shown) and displayed in the proper units to a user.

Increasing the pressure of compressed air increases the axial force applied to the specimen. However, since the piston 24 rides on a cushion of compressed air regardless of the pressure of the air, the negligible friction provided by the radial ball bearings remains the same regardless of how much axial force is applied to the specimen. This is a distinct advantage over prior art thrust bearing based devices in which increasing axial force results in an increasing frictional or torsional resistance to rotation. Thus, the twist induced in the specimen in response to the applied axial load can be accurately measured for axial loads up to and including a load that causes actual physical failure of the specimen.

The invention has been described herein in terms of a preferred embodiment. It will be clear to those of skill in the art, however, that various modifications, additions, deletions, and improvements might be made to the illustrated embodiment within the scope of the invention. For example, a simple gear train has been shown with the preferred embodiment coupling rotation of the piston to the optical encoder. This could, if desired, be replaced by a more elaborate gear train or other means for measuring rotation of the piston. The preferred embodiment has been illustrated as functioning through an increase in pressure below the piston to create a pressure differential. Obviously, such a differential could also be created by reducing the pressure within the upper region of the cylinder. Finally, compressed air has been illustrated as the operating medium in the preferred embodiment. Clearly, however, any suitable fluid might be used as an equivalent substitute including liquids or inert gases. These and numerous other additions, deletions, and modifications might well be made to the preferred embodiment illustrated herein without departing from the spirit and scope of the invention as set forth in the claims.

We claim:

1. A rotational displacement apparatus for applying an axial load to an extension-twist coupled specimen while allowing the specimen to twist freely in response to application of the axial load, said apparatus comprising:

a cylinder block having a top and a bottom and defining a substantially closed internal cylinder with a central axis;

a piston disposed within said cylinder, said piston having a piston rod that projects from said piston along said central axis through said bottom of said cylinder block to a free end adaptable for gripping one end of a material to be tested with the other end of the material being fixed at a location remote from said piston free end;

said piston defining a lower portion of said cylinder below said piston and an upper portion of said cylinder above said piston;

bearing means for rotatably securing said piston rod in said bottom of said cylinder block for free rotation of said piston within said cylinder;

means for delivering a compressed fluid to said lower portion of said cylinder to create a pressure differential between said lower portion of said cylinder and said upper portion of said cylinder for forcing said piston upwardly within said cylinder to apply an axial load to a specimen secured between said free end of said piston rod and a remote location;

said piston and said piston rod rotating freely in response to twisting induced in the specimen by the applied axial force so that the magnitude of twist can be measured accurately.

2. A rotational displacement apparatus as claimed in claim 1 and wherein said bearing means comprises at least one radial ball bearing mounted in said bottom of said cylinder block.

3. A rotational displacement apparatus as claimed in claim 1 and wherein said means for delivering a compressed fluid to said lower portion of said cylinder comprises a plurality of compressed fluid inlet ports communicating through said bottom of said cylinder block and means for delivering pressurized fluid to said inlet ports.

4. A rotational displacement apparatus as claimed in claim 3 and wherein said means for delivering pressurized fluid to said inlet ports comprises a bottom plate mounted to said bottom of said cylinder block and defining a plenum chamber therewithin the region of said compressed fluid inlet ports and a compressed fluid coupling formed in said bottom plate for coupling a remote source of compressed fluid with said plenum chamber.

5. A rotational displacement apparatus as claimed in claim 1 and wherein said piston is smaller than said cylinder to define a space between said piston and the walls of said cylinder and wherein said apparatus further comprises vent means for venting compressed fluid out of said upper portion of said cylinder, whereby compressed fluid delivered to said lower portion of said cylinder progressively escapes to the upper portion of the cylinder between the piston and the cylinder walls where it is vented so that the piston floats on and is supported by the compressed fluid delivered to the lower portion of the cylinder so that the piston and piston rod can rotate with negligible frictional resistance.

6. A rotational displacement apparatus as claimed in claim 5 and wherein the space between said piston and the walls of said cylinder is about 0.001 to 0.003 inches.

7. A rotational displacement apparatus as claimed in claim 1 and wherein the compressed fluid is compressed air.

8. A rotational displacement apparatus as claimed in claim 1 and further including means for detecting the degree of rotation induced in said piston by the twisting of the specimen.

9. A rotational displacement apparatus as claimed in claim 8 and wherein said means for detecting the degree of rotation induced in said piston comprises an optical encoder and means for coupling said optical encoder to rotational motion of said piston.

10. A rotational displacement apparatus as claimed in claim 9 and wherein said means for coupling said optical encoder to rotational motion of said piston comprises a gear shaft extending along said axis of said cylinder from the top thereof, said gear shaft being rotatably mounted within said top of said cylinder block and having a lower end configured to form a key, said piston being formed with a keyway extending along said axis of said cylinder and being sized and positioned for slidably receiving said key whereby rotation of said piston within said cylinder is transferred to said gear shaft, and means for transferring rotation of said gear shaft to said optical encoder.

11. A rotational displacement apparatus as claimed in claim 10 and wherein said means for transferring rotation of said gear shaft comprises a gear chain coupling said gear shaft to said optical encoder.

12. A device for applying axial tension to an extension-twist coupled specimen while allowing the specimen to twist freely under the influence of the applied tension, said device comprising:

a cylinder block defining a substantially closed internal cylinder;

a piston having a top side and a bottom side, said piston being movably disposed within said cylinder and having a piston rod extending out of said cylinder to a free end;

bearing means in said cylinder block guiding said piston rod for allowing said piston and said piston rod to be rotated;

clamp means on said free end of said piston rod for securely clamping one end of a specimen to be tested, the other end of the specimen being secured at a position remote from said free end; and means for causing a pressure differential between said top side of said piston and said bottom side of said piston to cause said piston to move within said cylinder and apply axial tension to the test strip, said piston and piston rod rotating as the strip twists allowing the degree of twist to be measured.

* * * * *